(12) United States Patent
Lampert

(10) Patent No.: US 7,338,284 B2
(45) Date of Patent: Mar. 4, 2008

(54) ENDODONTIC INSTRUMENT AND INSTRUMENT SYSTEM

(76) Inventor: Christopher J. Lampert, 712 Lake Forest Dr., Lake Oswego, OR (US) 97034

( * ) Notice: Subject to any disclaimer, the term of this patent is extended or adjusted under 35 U.S.C. 154(b) by 156 days.

(21) Appl. No.: 10/756,599

(22) Filed: Jan. 12, 2004

(65) Prior Publication Data

US 2004/0146832 A1    Jul. 29, 2004

Related U.S. Application Data

(60) Provisional application No. 60/439,479, filed on Jan. 13, 2003.

(51) Int. Cl.
*A61C 5/02* (2006.01)
(52) U.S. Cl. ...................... 433/102; 433/165
(58) Field of Classification Search ............... 433/102, 433/165, 166
See application file for complete search history.

(56) References Cited

U.S. PATENT DOCUMENTS

| | | | | |
|---|---|---|---|---|
| 1,022,838 | A * | 4/1912 | Funk | 433/102 |
| 2,436,325 | A * | 2/1948 | Penny | 407/18 |
| 3,894,339 | A * | 7/1975 | Manzi | 433/166 |
| 4,019,254 | A * | 4/1977 | Malmin | 433/102 |
| 4,836,780 | A * | 6/1989 | Buchanan | 433/102 |
| 4,850,867 | A | 7/1989 | Senia et al. | |
| 4,934,934 | A | 6/1990 | Arpaio et al. | |
| 4,990,088 | A | 2/1991 | Weissman | |
| 5,066,230 | A * | 11/1991 | Weissman | 433/165 |
| 5,257,934 | A * | 11/1993 | Cossellu | 433/102 |
| 5,628,674 | A | 5/1997 | Heath et al. | |
| 5,653,590 | A | 8/1997 | Heath et al. | |
| 5,752,825 | A | 5/1998 | Buchanan | |
| 5,882,198 | A | 3/1999 | Taylor et al. | |
| 6,074,209 | A | 6/2000 | Johnson | |
| 6,409,506 | B1 | 6/2002 | Graybill | |
| 6,712,611 | B2 | 3/2004 | Garman | |
| 2006/0228668 | A1 | 10/2006 | McSpadden | |

\* cited by examiner

*Primary Examiner*—John J Wilson
(74) *Attorney, Agent, or Firm*—Ganz Law, P.C.

(57) ABSTRACT

An endodontic file is provided for shaping and/or preparing a root canal. The file may include multiple cutting segments separated by non-cutting segments. The cutting segments are tapered and may have a cutting edge formed by plural helical flutes. Alternatively, the cutting segments may be formed of a substantially non-circular geometric shape with substantially straight cutting edges. The file is flexible and has increased resistance to cyclic fatigue breakage. The file further controls or limits which areas of the root canal are shaped and/or prepared during file use. The file may form part of a series of files to shape and/or prepare a root canal. Each file in the series may have cutting segments and non-cutting segments strategically placed in different regions along the working portion of the file to shape and/or prepare different portions of the root canal.

11 Claims, 5 Drawing Sheets

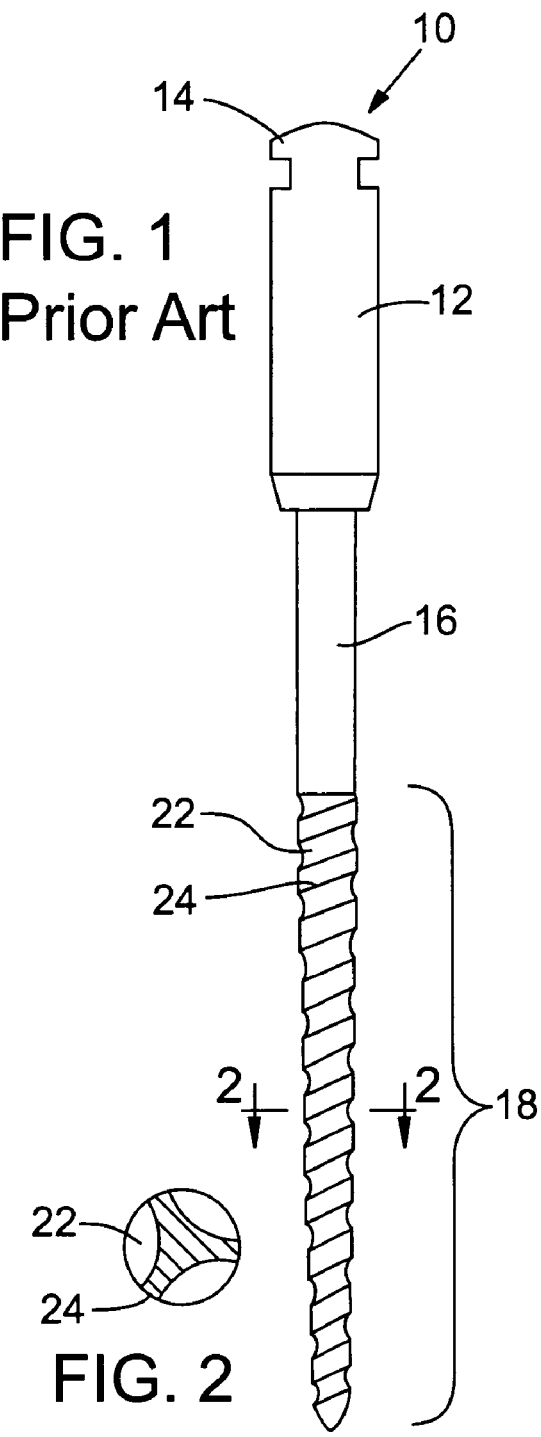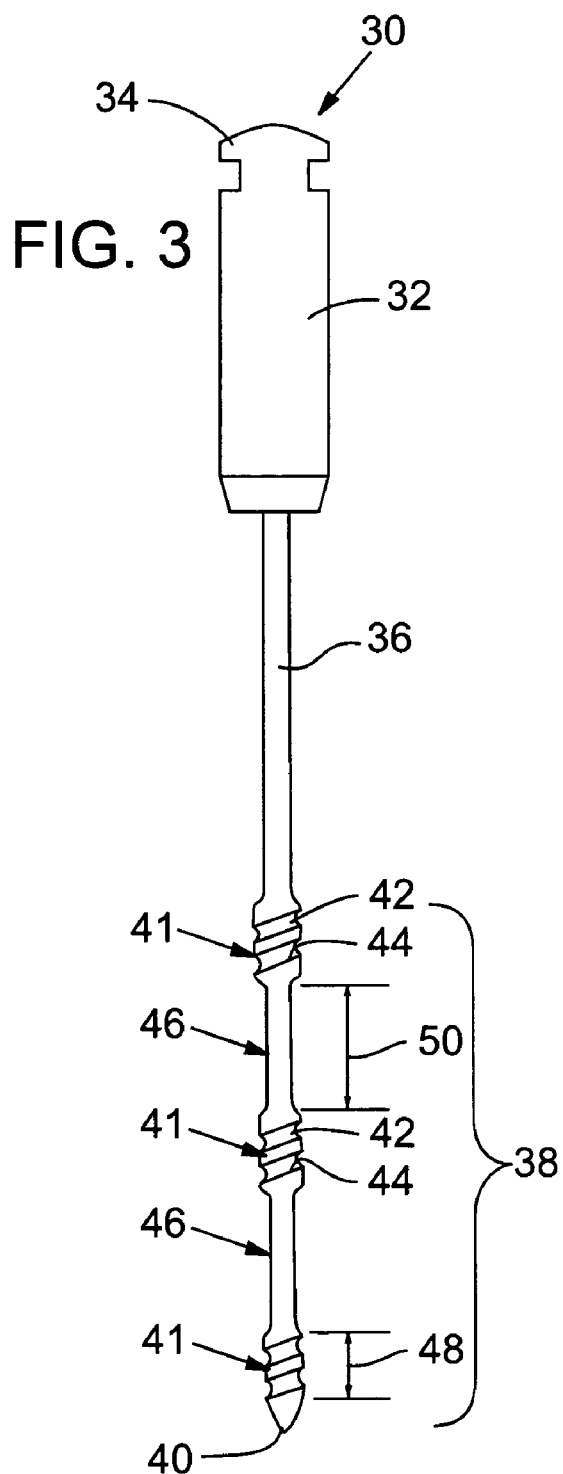

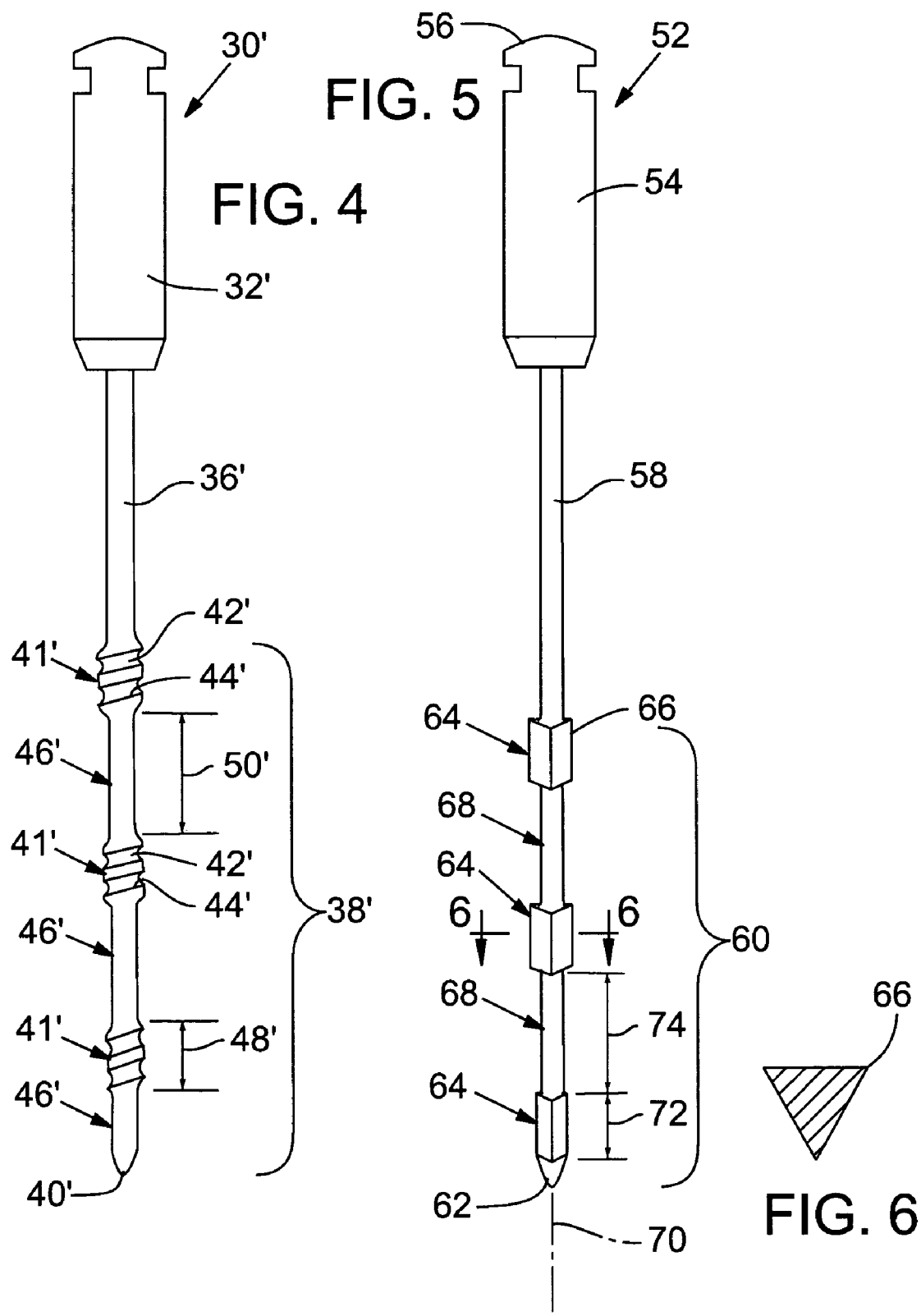

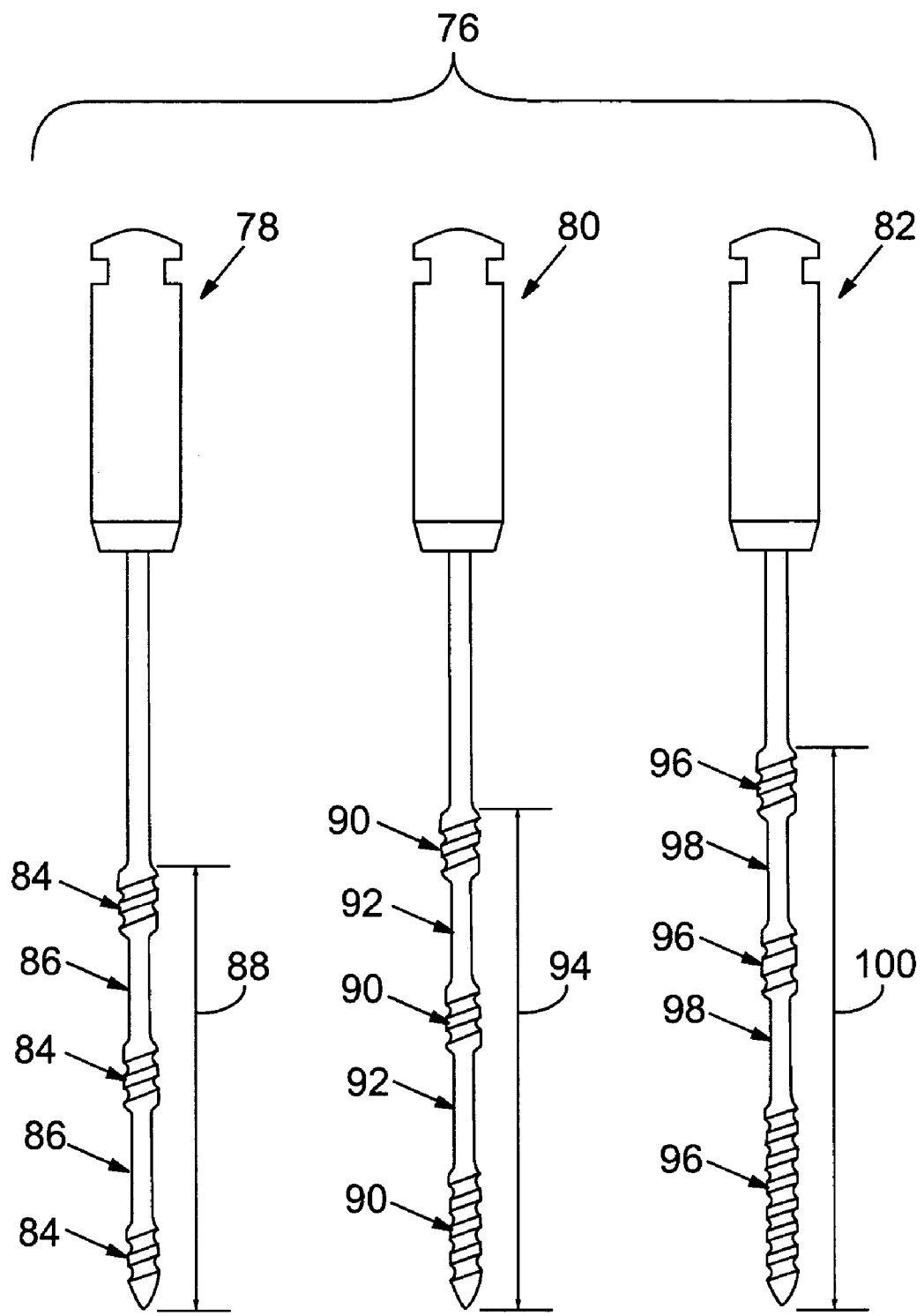

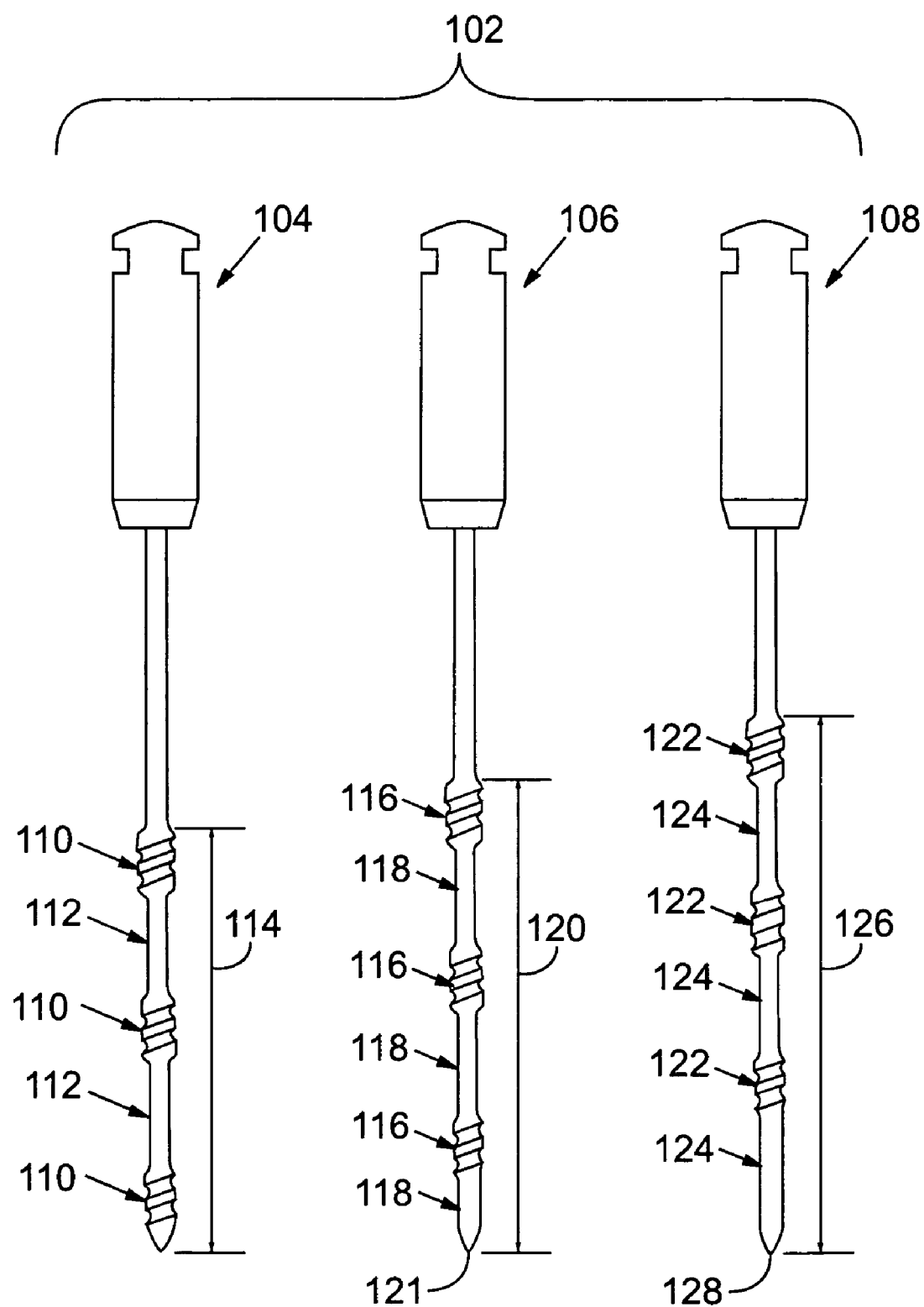

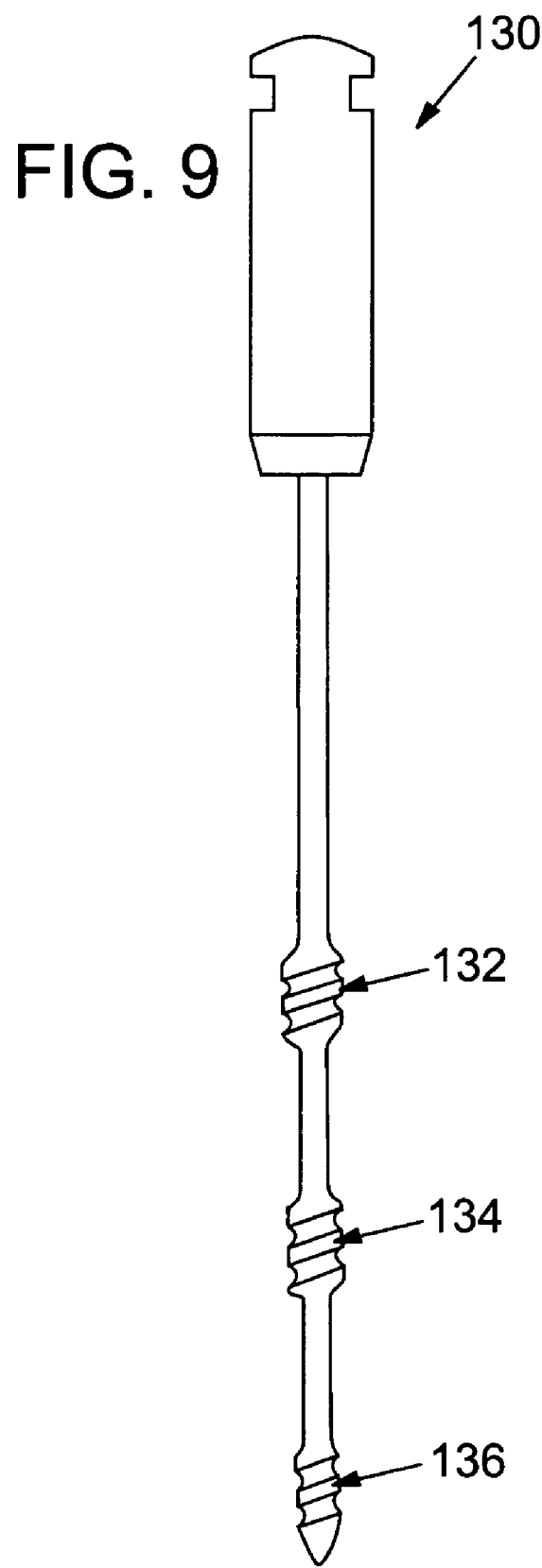

ENDODONTIC INSTRUMENT AND INSTRUMENT SYSTEM

This invention claims the benefit of co-pending U.S. Provisional Application No. 60/439,479, entitled "ENDODONTIC INSTRUMENT", filed Jan. 13, 2003, the entire disclosure of which is hereby incorporated by reference as if set forth in its entirety for all purposes.

BACKGROUND OF THE INVENTION

This invention relates generally to endodontic instruments known as endodontic files, used by dentists when performing root canal procedures. A root canal procedure is a common dental procedure for treating or preventing a dental abscess. During a root canal procedure, the infected nerve and pulpal tissue are removed from the root canal of the involved tooth. The root canal is then cleaned by shaping or reaming the root canal with endodontic files to produce a clean environment to receive a root canal filling material. The standard filling material, which has been used for over fifty years, is an inert material called gutta-percha.

Endodontic files are used to remove the contents of the root canal and to prepare or shape the root canal prior to filling it. Endodontic files may be designed to be manually manipulated by the fingers of a dentist or to be engine driven by a rotating hand piece, which rotates the file during use. Endodontic files typically consist of a tapered distal working portion containing a plurality of helical spiraled flutes, a shaft portion located proximal to the working portion, and a handle located on the proximal end of the instrument. The flutes form planing or cutting surfaces, which dislodge and remove the infected tissue within the root canal being treated. For all currently available tapered endodontic files the helical or spiral flutes turn continuously along the entire working portion of the file.

FIGS. 1 and 2 show a prior art endodontic file 10 that is representative of the type currently in use. File 10 includes a handle 12 at a proximal end 14, a shaft portion 16, and a working portion 18 that tapers toward a distal end 20. Working portion 18 is formed of a plurality of helical or spiral flutes 22 that form cutting surfaces 24 as seen most clearly in FIG. 2. Flutes 22 extend continuously along working portion 18. File 10 may be manipulated by hand or be engine driven to rotate so that cutting surfaces 24 remove infected tissue from the root canal.

Because root canals are seldom straight, but usually curved or twisted in multiple planes, it is important that endodontic files be flexible so that the file can follow the curved canal to its terminus during the cleaning process. Another advantage to having endodontic files with enhanced flexibility is that file breakage during the cleaning process of the root canal is greatly reduced. The recognized need for flexible endodontic files has led to the use of nickel-titanium alloys as the preferred material of choice for constructing endodontic files.

Understanding that file breakage during a root canal procedure is an undesired event and its prevention is critical to a successful root canal procedure, providing an endodontic file with a resistance to breakage would be of great benefit to the field of endodontics. File breakage generally occurs from two causes. The first cause is cyclic fatiguing of the instrument material caused by repeated bending of the file. The incidence of cyclic fatigue file breakage is inversely related to file flexibility, therefore as instrument flexibility increases, cyclic fatigue file breakage decreases. The second cause of file breakage is the application of excessive torque to the endodontic file leading to torque failure. Such excessive torque is caused, at least in part, by the fact that substantially the entire length of the file working portion is in contact with the canal wall.

Some current cleansing and shaping techniques used to prepare the root canal employ numerous endodontic files having a continuously tapered helical fluted working portion. The numerous files used during a root canal procedure may have different tip diameter sizes and/or tapers to allow the different files to clean different regions of the root canal. However, such current endodontic files encounter the problems discussed above.

Examples of prior art endodontic instruments are seen in U.S. Pat. Nos. 4,934,934; 5,628,674; 5,653,590; and 6,074,209, all of which are hereby incorporated by reference in their entireties for all purposes.

It would be an improvement in the art of endodontics to provide an endodontic file that has enhanced flexibility to reduce the likelihood of breakage. It would be a further improvement to provide an endodontic file having limited or dedicated cutting regions along the working portion of the file to limit the root canal surface area that is engaged by the endodontic file and to control which portion of the root canal is shaped and/or prepared. Decreasing the surface area of the endodontic file in contact with the root canal wall would effectively reduce the frictional torque applied to the instrument and would decrease the incidence of torque failure breakage

SUMMARY OF THE INVENTION

The present invention provides an endodontic file for shaping and/or preparing a root canal during a root canal procedure. The file has a proximal shaft portion connected to a handle portion and a distal working portion. The file may be manipulated by the fingers of an operator or inserted into a rotary engine driven hand piece. The unique working portion of the file may include multiple tapered cutting segments separated by non-cutting segments. The cutting segments have a cutting edge formed by a plurality of helical flutes. Each non-cutting segment preferably has a diameter that is significantly smaller than the diameter of the adjacent cutting segments. This arrangement provides overall flexibility of the file and increases the resistance to cyclic fatigue breakage. This arrangement further controls or limits which areas of the root canal are shaped and/or prepared during file use. The non-cutting segments limit the surface area of the root canal that is engaged by the cutting segments of the file. The cutting segments are located and arranged along the working portion to control which portion of the file actively shapes and/or prepares the root canal. The cutting segments may have a substantially continuous taper. Alternatively, the taper of each cutting segment may vary.

In another embodiment, the cutting segments may have a non-circular geometric configuration and may be formed as straight and oriented substantially parallel to the long axis of the file rather than formed as helical or spiraling cutting segments. This embodiment prevents the file from self-feeding into the root canal.

In another embodiment, the endodontic file forms part of a series of endodontic files to shape and/or prepare a root canal. Each file in the series may have cutting segments and non-cutting segments strategically placed in different regions along the working portion of the file to allow each file in the system to shape and/or prepare different portions of the root canal.

The present invention provides an endodontic file for use in root canal treatment in which the cutting segments are located along the working portion in a manner to correspond with a portion of a root canal that is to be actively cut. The cutting segments and non-cutting segments may be of any length and may by of any number.

The non-cutting segments have a diameter that is substantially less than the diameter of the cutting segments in order to provide flexibility and to control which region of the root canal is shaped or prepared by the file.

These and other embodiments are described in more detail in the following detailed descriptions and the figures.

The foregoing is not intended to be an exhaustive list of embodiments and features of the present invention. Persons skilled in the art are capable of appreciating other embodiments and features from the following detailed description in conjunction with the drawings.

BRIEF DESCRIPTION OF THE DRAWINGS

FIG. 1 is a view of a prior art endodontic file.

FIG. 2 is a cross-sectional view of the endodontic file of FIG. 1 taken along line A-A.

FIG. 3 is a view of one embodiment of an endodontic file of the present invention having multiple tapered cutting sections.

FIG. 4 is a view of another embodiment of an endodontic file of the present invention having a non-cutting section at the distal end of the file.

FIG. 5 is a view of another embodiment of an endodontic file having straight cutting sections.

FIG. 6 is a cross-sectional view of the endodontic file of FIG. 5 taken along line B-B.

FIG. 7 is a view of an endodontic file system comprised of plural endodontic files each having cutting sections located at different locations along the working portion of the file.

FIG. 8 is a view of another embodiment of an endodontic file system showing an alternative arrangement of cutting sections along the working portion of the file.

FIG. 9 is a view of another embodiment of an endodontic file in which each cutting segment has a different taper.

DETAILED DESCRIPTION OF THE INVENTION

Representative embodiments of the present invention are shown in FIGS. 3-9, wherein similar features share common reference numerals.

FIG. 3 shows one embodiment of an endodontic file 30 of the present invention. File 30 may include a handle 32 located at a proximal end 34, a shaft 36, and a working portion 38 extending to a distal end 40. Working portion 38 may be formed of a plurality cutting segments 41 formed of helical or spiral flutes 42 that form cutting edges 44 and separated by non-cutting segments 46. Cutting segments 41 may be of any desired shape but are shown in this embodiment as being tapered in a direction from proximal end 34 toward distal end 40. Non-cutting segments 46 are shown in this embodiment to have a smooth circular cross-section having a diameter that is less than the diameter of the adjacent cutting segments 41. The relationship between cutting segments 41 and non-cutting segments 46 provide flexibility to file 30 to eliminate or reduce the chance of breakage as working portion 38 follows any curved and/or twisted portions of the root canal.

In addition to providing flexibility, file 30 provides control over which portion or portions of the root canal are shaped and/or prepared. This is accomplished by the location of cutting segments 41 along working portion 38. Cutting segments 41 may be located along working portion 38 at selected locations depending on which areas of the root canal are to be shaped and/or prepared. For example, in the embodiment of FIG. 3, only the portions of the root canal adjacent cutting segments 41 are shaped and/or prepared. The embodiment of file 30 shown in FIG. 3 shows cutting segments 41 located along working portion 38 in a spaced arrangement in which a cutting segment 41 is located at distal end 40. FIG. 4 shows another embodiment of an endodontic file similar to file 30 of FIG. 3 in which like parts will be given like reference numbers indicated with a prime ('). Thus, file 30' includes cutting segments 41' located and arranged along working portion 38' so that a non-cutting segment 46' is located at distal end 40'. It should be further noted that other aspects of working portion 38, 38' may vary. For example, although only three cutting segments 41, 41' are shown in FIGS. 3 and 4, the number of cutting segments 41, 41' may vary. Additionally, the length 48, 48' of cutting segments 41, 41' and/or the length 50, 50' of non-cutting segments 46, 46' may vary.

FIGS. 5 and 6 show another embodiment of a file 52 that includes a handle 54 located at a proximal end 56, a shaft portion 58, and a working portion 60 extending to a distal end 62. Working portion 60 may be formed of a plurality cutting segments 64 each having a geometrical shape that forms a cutting edge 66 and separated by non-cutting segments 68. In this embodiment, cutting segments 64 may have a non-circular shape and are shown as being triangular (FIG. 6). However, it should be understood by those skilled in the art that the invention is not limited to cutting segments having a triangular shape and that other geometric shapes may be contemplated. Preferably, the geometric shape of cutting segments 64 form cutting edges 66 that are substantially parallel to the long axis 70 of file 52. Non-cutting segments 68 are shown in this embodiment to have a smooth circular cross-section having a diameter that is less than the cross-sectional shape of the adjacent cutting segments 64. Cutting segments 64 have a length 72 and non-cutting segments 68 have a length 74 both of which may vary. The relationship between cutting segments 64 and non-cutting segments 68 provide flexibility to file 30 to eliminate or reduce the chance of breakage as working portion 60 follows any curved and/or twisted portions of the root canal.

FIG. 7 shows a file system 76 that includes a series of individual files 78, 80, and 82 being of substantially equal length, each file having cutting segments and non-cutting segments strategically located along the file to allow each file to shape and/or prepare a different region of the root canal and to divide the workload of shaping and/or preparing the root canal among the files in the file system 76. For example, in the embodiment shown in FIG. 7, file 78 may include multiple cutting segments 84 separated by non-cutting segments 86 located along working portion 88. File 80 may include cutting segments 90 and non-cutting segments 92 located along working portion 94. Working portion 94 extends over a greater portion of file 80 than working portion 88 of file 78. Additionally, the lengths of cutting segments 90 and non-cutting segments 92 may vary so that they may overlap with cutting segments 84 and non-cutting segments 86 of file 78. File 82 may have cutting segments 96 and non-cutting segments 98 located along working portion 100, which extends over a greater portion of file 82 than working portion 94 of file 80 or working portion 88 of file 78. In a manner similar to files 78 and 80, the length of cutting segments 96 and non-cutting segments 98 may vary so that they may overlap with cutting segments 90 and non-cutting segments 92 of file 80 and cutting segments 84 and non-cutting segments 86 of file 78. The cutting segments 84, 90, 96 of individual files 78, 80, 82 are arranged so that, when taken together, they effectively form one continuous cutting segment covering the entire working portion 100.

FIG. 8 shows an alternative file system 102 that includes a series of individual files 104, 106, and 108 being of substantially equal length. Similar to files 78, 80, 82 in FIG. 7, each file 104, 106, 108 have cutting segments and non-cutting segments strategically located along the file to allow each file to shape and/or prepare a different region of the root canal and to divide the workload of shaping and/or preparing the root canal among the files in the file system 102. However, the cutting segments and non-cutting segments of files 104, 106, 108 are arranged in an alternative manner. For example, file 104 may include multiple cutting segments 110 separated by non-cutting segments 112 located along working portion 114. File 106 may include cutting segments 116 and non-cutting segments 118 located along working portion 120 so that a non-cutting segment 118 is located at distal end 121. Working portion 120 extends over a greater portion of file 106 than working portion 114 of file 104. Additionally, the lengths of cutting segments 116 and non-cutting segments 118 may vary so that they may overlap with cutting segments 110 and non-cutting segments 112 of file 104. File 108 may have cutting segments 122 and non-cutting segments 124 located along working portion 126, which extends over a greater portion of file 108 than working portion 120 of file 106 or working portion 114 of file 104. A non-cutting segment 124 is located at a distal end 128. In a manner similar to files 104 and 106, the length of cutting segments 122 and non-cutting segments 124 may vary so that they may overlap with cutting segments 116 and non-cutting segments 118 of file 106 and cutting segments 110 and non-cutting segments 112 of file 104. The cutting segments 110, 116, 122 of individual files 104, 106, 108 are arranged so that, when taken together, they effectively form one continuous cutting segment covering the entire working portion 126. The staggered cutting segments and non-cutting segments of the files of each system 76, 102 have been described as overlapping. However, it is within the scope of this invention that the staggered cutting segments of the related files in each system 76, 102 do not overlap. Regardless of whether or not the cutting segments overlap the files in both systems 76, 102, when taken together, form a cutting segment along the entire working portion.

FIG. 9 shows an alternative embodiment for a file 130 having variable tapered cutting segments for added flexibility. In this embodiment, the percentage taper of one cutting segment may be different from the percentage taper of the other cutting segments. For example, first cutting segment 132 may have an 8% taper, second cutting segment 134 may have a 6% taper, and third cutting segment 136 may have a 4% cutting taper.

It should be understood by those skilled in the art that either file system 76, 102 may be comprised of files having tapered cutting segments, variable tapered cutting segments, or geometrically shaped cutting segments.

Persons skilled in the art will recognize that many modifications and variations are possible in the details, materials, and arrangements of the parts and actions which have been described and illustrated in order to explain the nature of this invention and that such modifications and variations do not depart from the spirit and scope of the teachings and claims contained therein.

While the inventor understands that claims are not a necessary component of a provisional patent application, and therefore has not included detailed claims, the inventor reserves the right to claim, without limitation, at least the following subject matter.

What is claimed:

1. An endodontic file system, comprising a plurality of endodontic files for use in root canal treatment, each endodontic file comprising: an elongated shank having a long axis with a proximal end connected to a handle adapted to be manipulated by hand or inserted into a rotary drive, and a working portion extending to a distal end, the working portion including a plurality of alternating cutting segments and non-cutting segments that are spaced proximally to distally to each other along the working portion, wherein the cutting segments and non-cutting segments on each endodontic file are located along the working portion in a position different from the location of the cutting segments and non-cutting segments of the other endodontic files in the system.

2. The endodontic file system of claim 1, wherein the cutting segments of each file include a plurality of helical extended flutes that form a cutting edge.

3. The endodontic file system of claim 1, wherein the cutting segments of each file decrease in diameter from the proximal end of the shank to the distal end of the working portion.

4. The endodontic file system of claim 1, wherein the cutting segments of each file are tapered in a direction toward the distal end of the working portion.

5. The endodontic file system of claim 1, wherein the taper of each cutting segment on a file is different from the taper of the other cutting segments on the same file.

6. The endodontic file system of claim 1, wherein each file has a cutting segment that includes a convex portion.

7. The endodontic file system of claim 1, wherein the non-cutting segments of each file have a diameter substantially less than the diameter of the cutting segments.

8. The endodontic file system of claim 1, wherein the non-cutting segments of each file have a substantially round cross-section.

9. The endodontic file system of claim 1, wherein the cutting segments of each file include a cutting edge that is substantially parallel with the long axis of the file and not helically spiraled.

10. The endodontic file system of claim 1, wherein the non-cutting segments have a substantially non-round cross section.

11. A method of performing a root canal procedure, comprising: providing a plurality of endodontic files, each file having a working portion with a plurality of alternating cutting segments spaced proximally to distally to each other along the working portion and separated by non-outing segments, wherein the cutting segments and non-cutting segments on each endodontic file are located along the working portion in a position different from the location of the cutting segments and non-cutting segments of the other endodontic files in the plurality, and using the plurality of files in an endodontic procedure.

* * * * *